United States Patent [19]

Yasohama et al.

[11] Patent Number: 5,432,444
[45] Date of Patent: Jul. 11, 1995

[54] INSPECTION DEVICE HAVING COAXIAL INDUCTION AND EXCITING COILS FORMING A UNITARY COIL UNIT

[75] Inventors: Kazuhiko Yasohama; Hiroaki Kohama; Hirofumi Takahashi, all of Tokyo, Japan

[73] Assignee: Kaisei Engineer Co., Ltd., Tokyo, Japan

[21] Appl. No.: 61,504

[22] Filed: May 14, 1993

Related U.S. Application Data

[63] Continuation of Ser. No. 780,299, Oct. 22, 1991, abandoned.

[30] Foreign Application Priority Data

| Oct. 23, 1990 | [JP] | Japan | 2-283368 |
| Oct. 2, 1991 | [JP] | Japan | 3-255597 |
| Oct. 2, 1991 | [JP] | Japan | 3-255598 |

[51] Int. Cl.⁶ ............................................ G01N 27/82
[52] U.S. Cl. .................................. 324/240; 324/228; 324/239; 324/207.17
[58] Field of Search ............. 324/207.16, 207.17, 324/228–243

[56] References Cited

U.S. PATENT DOCUMENTS

| 2,971,151 | 2/1961 | Mierendorf et al. | 324/239 X |
| 3,165,691 | 1/1965 | McClanahan | 324/239 |
| 3,588,683 | 6/1971 | Lloyd | 324/241 X |
| 3,686,564 | 8/1972 | Mallick, Jr. et al. | 324/243 X |
| 3,848,466 | 11/1974 | Dial et al. | 324/233 X |
| 4,010,536 | 3/1977 | Fujita et al. | 324/239 X |
| 4,053,828 | 10/1977 | Ambler et al. | 324/239 |
| 4,079,312 | 3/1978 | Osborn et al. | 324/242 X |
| 4,134,538 | 1/1979 | Lagarde et al. | 324/239 X |
| 4,423,377 | 12/1983 | Podhrasky | 324/239 X |
| 4,470,015 | 9/1984 | Hirschi et al. | 324/239 X |
| 4,555,665 | 11/1985 | Stanley et al. | 324/239 X |
| 4,563,644 | 1/1986 | Lenander et al. | 324/239 X |
| 4,563,645 | 1/1986 | Kerr | 324/239 X |
| 4,590,431 | 5/1986 | Anderson et al. | 324/239 X |
| 4,659,989 | 4/1987 | Kerr | 324/239 X |
| 4,675,603 | 6/1987 | Rajakovics | 324/239 X |
| 4,779,048 | 10/1988 | Aichele | 324/239 X |
| 4,804,912 | 2/1989 | Lysen | 324/207.17 |
| 4,818,936 | 4/1989 | Kemlo | 324/233 X |

Primary Examiner—Sandra L. O'Shea
Assistant Examiner—Warren S. Edmonds
Attorney, Agent, or Firm—Wenderoth, Lind & Ponack

[57] ABSTRACT

An inspection device has an exciting coil for generating an electromagnetic field and an induction coil which are integrally connected to each other a coaxial relation so as to induce mutual inductance in the induction coil by the electromagnetic field. The mutual inductance caused in the induction coil varies with a given object to be inspected which is present in the electromagnetic field. The object can be inspected by analyzing the change in inductance.

5 Claims, 7 Drawing Sheets

F I G. 11
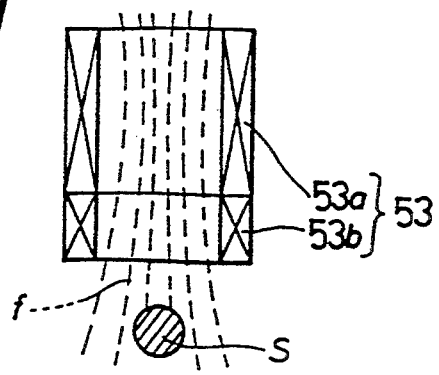
F I G. 12
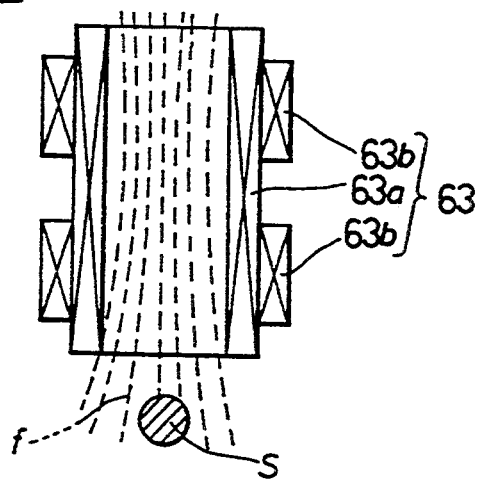
F I G. 13
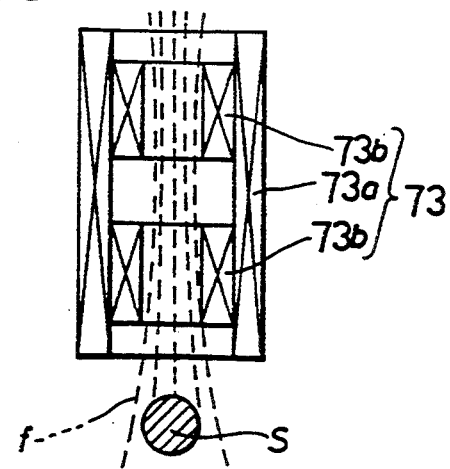

INSPECTION DEVICE HAVING COAXIAL INDUCTION AND EXCITING COILS FORMING A UNITARY COIL UNIT

This application is a continuation of now abandoned application, Ser. No. 07/780,299, filed Oct. 22, 1991, now abandoned.

BACKGROUND OF THE INVENTION

1. Field of the Invention

This invention relates to an inspection device using electromagnetic induction for detecting an abnormality in an object to be inspected, and more particularly, to a device for inspecting given objects of all kinds such as foods, medicinal tablets, synthetic resin products and various workpieces, using a change in electromagnetic induction to detect foreign matter or defects in the object.

2. Description of the Prior Art

Magnetic flux changes with the existence of an object in an electromagnetic field, thereby changing the inductance of a coil placed in the electromagnetic field. The inductance of the coil changes proportionally with the dielectric constant, magnetic permeability, size, relative position and other possible inductive factors of the object located in the electromagnetic field. When some of the inductive factors of the object located in the electromagnetic field are known, the other unknown factors can be exactly calculated from the detected change of the inductance. A variety of non-destructive inspection devices using such principles of electromagnetic induction are known for recognition of the existence or identification of given objects.

One of the typically known inspection devices of this type is shown in FIG. 1. This inspection device comprises an electromagnetic coil 1 (self-induction coil) which generates an electromagnetic field with an alternating current and is provided in one arm of a bridge circuit 2. In the bridge circuit, a pair of resistors R1 and R2 are equal in impedance to each other. When the coil 1 is excited in the normal state in which no substance exists in the electromagnetic field induced by applying an alternating current from a power source 3 to the coil, the inductance of coil 1 is in inductance equal in inductance to an adjacent inductor L, and therefore, the bridge circuit 2 on the whole is in equilibrium. In this steadily balanced state, a measuring instrument 4 (usually a galvanometer or sensitive microammeter) connected to diagonal output points P1, P2 of the bridge circuit 2 generates no output (Vout=0).

However, when a object S is located in the electromagnetic field induced by the coil 1, the self-inductance of the coil 1 varies with the coefficient of induction of the object S, thereby breaking the balanced state of the bridge circuit, resulting in an output voltage Vout across the output points P1 and P2.

By analyzing the change in output voltage appearing from the bridge circuit, the physical properties, size, location and other specific features of the given object S to be inspected can be recognized accurately. Furthermore, it is even possible to determine the speed of the object S moving in the electromagnetic field induced by the coil. Also foreign matter or impurities possibly contained in the given object can be detected by comparison with a standard specimen equivalent to the given object. In this case, the standard specimen is arranged in the electromagnetic field induced by the inductor L, so that the bridge circuit 2 assumes its balanced stat when a faultless object is placed in the electromagnetic field induced by the coil.

The aforementioned inspection device is commonly called a "self-induction type" inspection device.

Another type of known inspection device uses mutual induction as shown in FIG. 2. This inspection device comprises an exciting coil 6 (primary coil) excited by a power source 5 to generate an electromagnetic field and a pair of detection coils 7a, 7b (secondary coil) which acquires the electromagnetic field (magnetic flux) generated by the exciting coil 6 and inducing an electromotive current, and a differential amplifier 8. The detection coils 7a, 7b are wound in opposite directions to each other and are differentially connected in series, so that the electromotive currents induced in the respective detection coils 7a, 7b by the electromagnetic field from the exciting coil 6 cancel each other in the normal equilibrium state. That is to say, in the equilibrium state of the detection coils 7a and 7b, the differential voltage across the output points P1 and P2 becomes zero, i.e. Vout=0.

In general, the mutual induction inspection device has an inspection path 9 between the exciting coil 6 and paired detection coils 7a, 7b for allowing a testing object S to pass therethrough across the magnetic flux f brought about by the exciting coil 6. When passing the testing object S through the path 9 across the magnetic flux induced by the exciting coil 6, the magnetic flux which reaches the detection coils 7a, 7b undergoes a change in interlinkage. Namely, the paired detection coils 7a, 7b respectively acquire different interlinkage numbers of the magnetic flux, to thereby break the balanced state of the detection coils 7a, 7b (nonequilibrium state). As a result, a differential voltage Vout is generated from the differential amplifier 8. Thus, it is possible to recognize the quantity and size of the object S or to detect a defect in the object S.

In the prior art inspection devices noted above, since the nonequilibrium state in electromagnetic induction is determined using the differential voltage derived from the bridge circuit 2 or the series connected detection coils 7a, 7b, the change in induced electromotive current brought about by passing the object across the magnetic flux must be detected with a remarkably high accuracy in order to increase the measurement accuracy.

In the self-induction inspection device illustrated in FIG. 1, however, because the rate of change in self-induction (difference between the base inductance and the inductance undergoing a change) is very small, it has been substantially impossible or difficult to accurately detect such a small change in inductance. Thus, the conventional inspection device of the self-induction type has a low sensitivity and can not be applied to inspect measuring objects having a low rate of change in inductance and nonmetallic objects such as of synthetic resin.

On the other hand, the mutual induction inspection device has the inspection path 9 located between the exciting coil 6 (primary coil) and paired detection coils 7a, 7b (secondary coil). The induction efficiency is in inverse proportion to the dimension of the inspection path 9 (distance d from the exciting coil to the paired detection coils). This device is disadvantageous in that the inspection path 9 is limited in dimension from the standpoint of performance and adds to the size in total system size and prevents a large measuring object from passing therethrough.

Even if the inspection path is widened for permitting such a large object to pass therethrough, the inspection accuracy would be decreased proportionally and a slight change in induction could not be detected.

Moreover, the inspection device of the mutual induction type inevitably has a fatal disadvantage in that, when the object S approaches one of the paired detection coils (coil 7a in FIG. 2), not only the coil 7a but also the coil 7b is affected by the object S to cause the coil 7b to vary in inductance. Though either of the detection coils should have, as a reference inductor, a fixed inductance relative to the other coil close to the object S, both the coils vary in inductance even when the object S approaches one of the detection coils. Namely, the induction of the detection coil remote from the object S varies in a complicated manner with the relative position of the object S to the detection coils. Therefore, a change in inductance of one of the detection coils cannot be determined accurately, resulting in a conspicuous decrease in measuring accuracy.

As noted above, the conventional inspection devices using electromagnetic induction are restricted in the size of the object to be inspected and inevitably lead to noticeable measurement errors.

OBJECT OF THE INVENTION

This invention is made to eliminate the drawbacks suffered by the conventional inspection devices as described above and has an object to provide an inspection device using electromagnetic induction, capable of inspecting or detecting all sorts of objects irrespective of the material thereof including dielectric substances and magnetic substances with a notably high accuracy and sensitivity.

Another object of this invention is to provide a simple and high performance inspection device capable of effecting identification of objects such as foods, medicinal tablets, synthetic resin products and various workpieces regardless of the size of the objects and detecting abnormalities such as defects in the object.

SUMMARY OF THE INVENTION

To attain the object described above according to this invention, there is provided an inspection device using electromagnetic induction, comprising a detection coil unit including an exciting coil for generating an electromagnetic field with an alternating current, and at least one induction coil integrally connected coaxially to the exciting coil, and a decision unit for detecting a change in induction of the induction coil.

The induction coil acquires magnetic flux of the electromagnetic field generated by the exciting coil, to induce an electromotive current. The inductance of the induction coil undergoes a change with the interlinkage number of magnetic flux which is changed by placing an object in the electromagnetic field generated by the exciting coil. The change of the inductance is detected and analyzed by the decision unit such as a balance circuit, a comparator, a differential amplifier and an identifying circuit, so that the given objects can be inspected with a high accuracy.

The detection coil unit is composed by integrally disposing the induction coil inside or outside the exciting coil or coaxially arranging the induction coil and exciting coil side by side. Thus, by integrally assembling the exciting coil and induction coil, the mutual induction between these coils can be efficiently effected to increase the sensitivity and decrease the size of the inspection device. Since the object to be measured is placed outside the detection coil, the size of the object is not restricted, and therefore, any large object can be measured.

Other and further objects of this invention will become obvious upon an understanding of the illustrative embodiments described and the appended claims, and various advantages not referred to herein will occur to one skilled in the art upon employment of the invention in practice.

BRIEF DESCRIPTION OF THE DRAWINGS

FIG. 11 is a schematic view showing a sixth embodiment of this invention.

FIG. 12 is a view showing a seventh embodiment of this invention.

FIG. 13 is a view showing an eighth embodiment of this invention.

DESCRIPTION OF THE PREFERRED EMBODIMENTS

The present invention will become more fully understood from the detailed description given hereinbelow and the accompanying drawings which are given by way of illustration only, and thus are not limitative of this invention.

Figure 1:
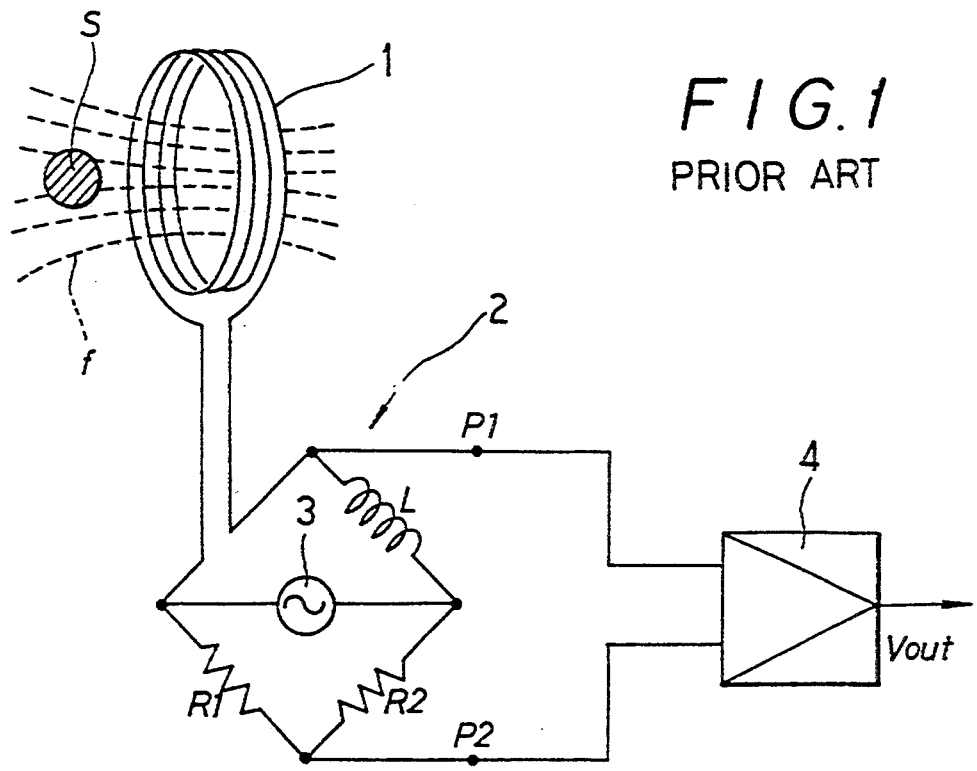
FIG. 1 is a schematic view showing a prior art inspection device using electromagnetic induction.
Figure 2:
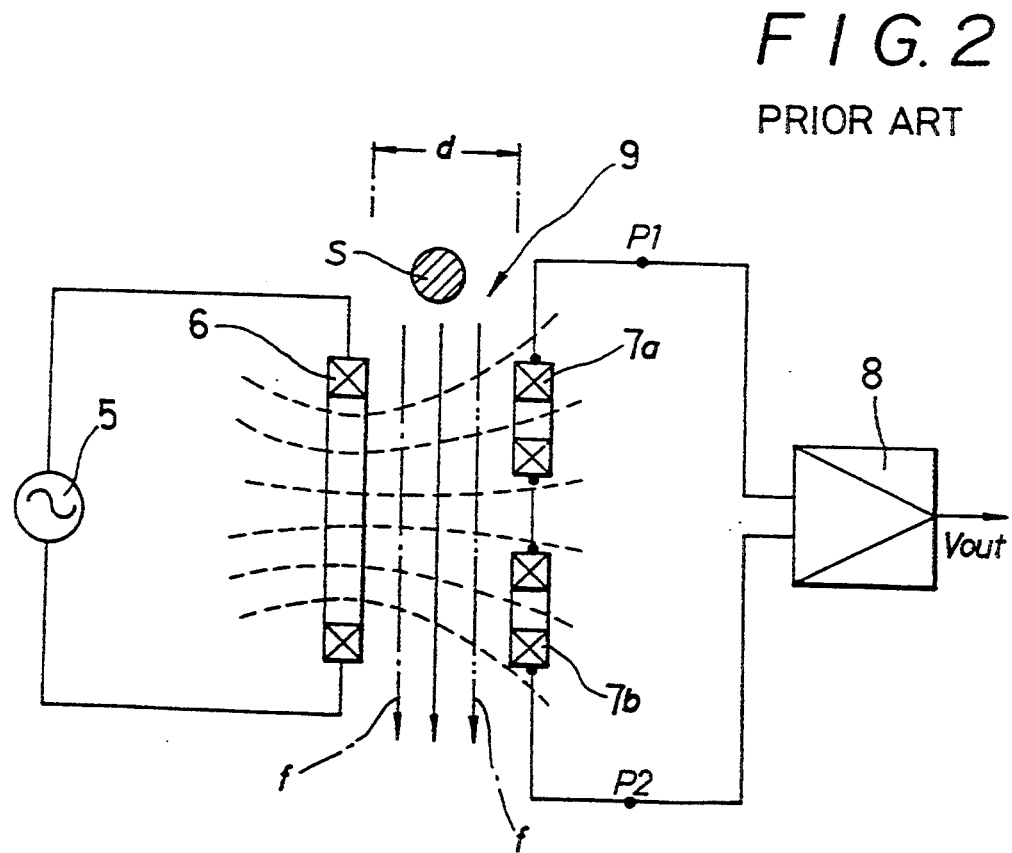
FIG. 2 is a schematic view showing another prior art inspection device using electromagnetic induction.
Figure 3:
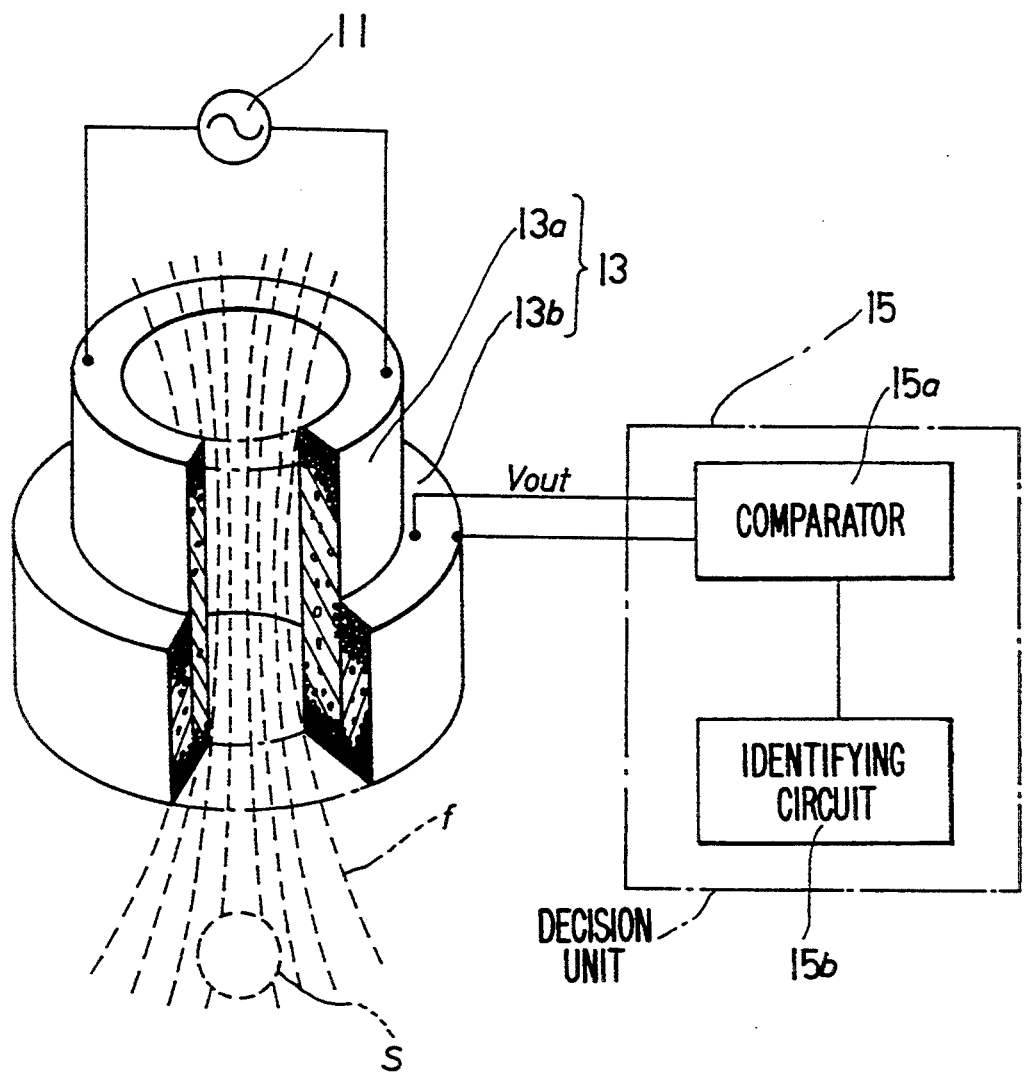
FIG. 3 is a schematic view showing a first embodiment of the inspection device according to this invention.

FIG. 3 illustrates schematically one embodiment of the inspection device using electromagnetic induction according to this invention. This inspection device comprises a power source 11, a detection coil unit 13 serving to form an electromagnetic field in which an object S to be inspected is placed and to simultaneously generate an electromotive current induced therein by the electromagnetic field, and a decision unit 15 for analyzing the electromotive current from the detection coil unit 13.

The detection coil unit 13 is composed of an exciting coil 13a for generating the alternating electromagnetic field (magnetic flux f) with the application of an alternating current from the power source 11, and an induction coil 13b intimately wound round the outer periphery of one half portion of the exciting coil 13a, so as to induce therein electromotive current (electromotive force) caused by the electromagnetic field generated by the exciting coil 13a. Thus, since the exciting coil 13a as a primary coil and the induction coil 13b as a secondary coil are integrated, the induction coil 13b acquires all the magnetic flux f, giving rise to mutual inductance with high efficiency to induce electromotive force (output signal Vout) with sufficient intensity.

When the object S to be inspected is placed in the electromagnetic field (magnetic flux f) generated by the exciting coil 13a as illustrated, the magnetic flux f undergoes a change, resulting in a change in inductance of the induction coil 13b. The change of the inductance of the induction coil 13b varies according to the material, size and other factors of the given object S. Even if the change in inductance is very small, it can be detected with high sensitivity because the exciting coil 13a and induction coil 13b are intimately integrated.

By comparing the inductance of the induction coil 13b when the object S exits in the electromagnetic field with the basic inductance thereof when no object exits therein, not only can the existence of the object S be recognized but also the size and material can be measured accurately. Also, even a fine foreign substance possibly contained in the measuring object S can be detected with precision.

The decision unit 15 has a function of analyzing the output signal Vout from the induction coil 13b. In this embodiment, the decision unit 15 comprises a comparator 15a for comparing the output signal (Vout) from the induction coil 13b with the reference value (Vref) which is predetermined from the inductance of the induction coil 13b in the normal state in which no object is present in the electromagnetic field induced by the exciting coil 13a, and an identifying circuit 15b for identifying the given object S on the basis of a dfferential signal outputted from the comparator 15a.

Figure 4:
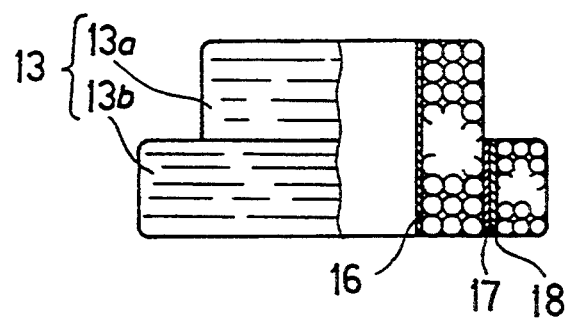
FIG. 4 is a partially cutaway side view showing the detection coil unit in FIG. 3.

As shown in FIG. 4, the detection coil unit 13 is made by first winding a conductive wire on a bobbin 16 to form the exciting coil 13a shaped in the form of a cylinder, wrapping an electromagnetic shielding layer 17 and an insulating sheet 18 around a part of the outer periphery of the exciting coil 13a, and further winding a conductive wire round the insulating sheet 18 to form the induction coil 13b. The bobbin 16 may be removed upon placing the detection coil unit 13 to use. This method of forming the detection coil and the components and arrangement of the exciting coil and induction coil should not be understood as limitative.

Figure 5:
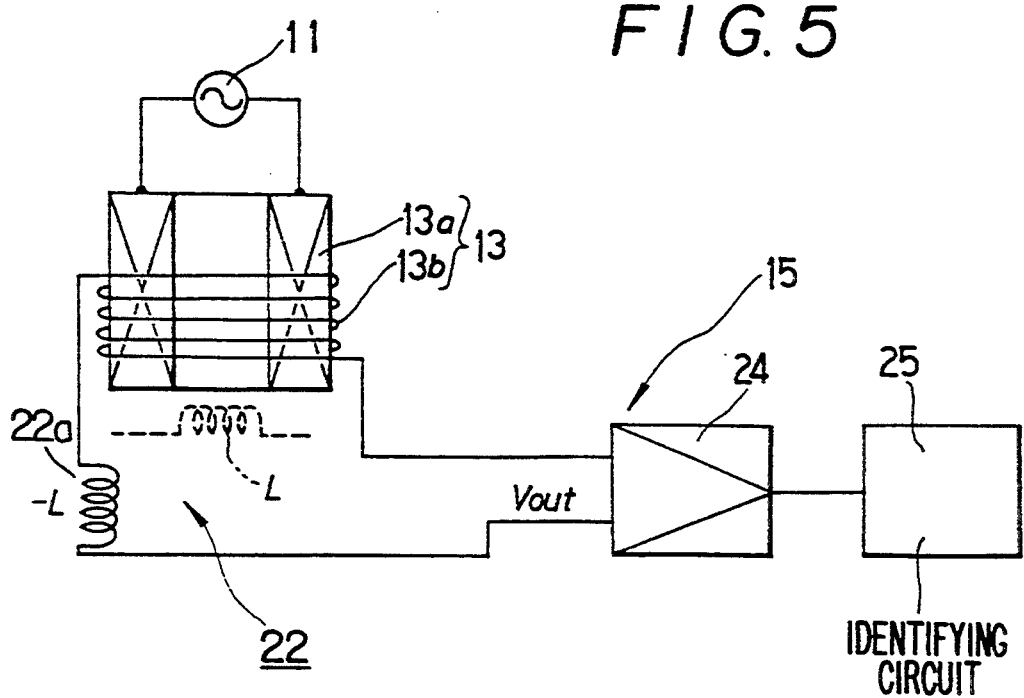
FIG. 5 is a schematic view showing a second embodiment of this invention.

The decision unit 15 in the second embodiment shown in FIG. 5 includes a balance circuit 22, a differential amplifier 24, and an identifying circuit 25. This decision unit 15 can be deemed electrically equivalent to the decision unit in FIG. 3.

In the balance circuit 22, the induction coil 13b serves as a real number element (L) and maintains equilibrium relative to an inductor 22a serving as an imaginary number element ($-L$) in a steady state in which the electromagnetic field generated by the exciting coil 13a is not affected by any other substance. That is, in the steadily balanced state, the inductance of the induction coil 13b which is induced by the electromagnetic field generated by the exciting coil 13a is canceled by the specific inductance of the inductor 22a so that the differential output voltage Vout from the balance circuit 22 becomes substantially zero (Vout=0). However, when the electromagnetic field generated by the exciting coil 13a is affected by an object, the inductance L of the induction coil 13b varies to cause the difference in inductance between the induction coil 13b and the inductor 22a. The difference in inductance results in a differential voltage Vout which is fed to the identifying circuit 25 via the amplifier 24. By setting the reference value (criterion) in the identifying circuit 25 in advance, a specification test for standardizing various products can be easily carried out.

Figure 6:
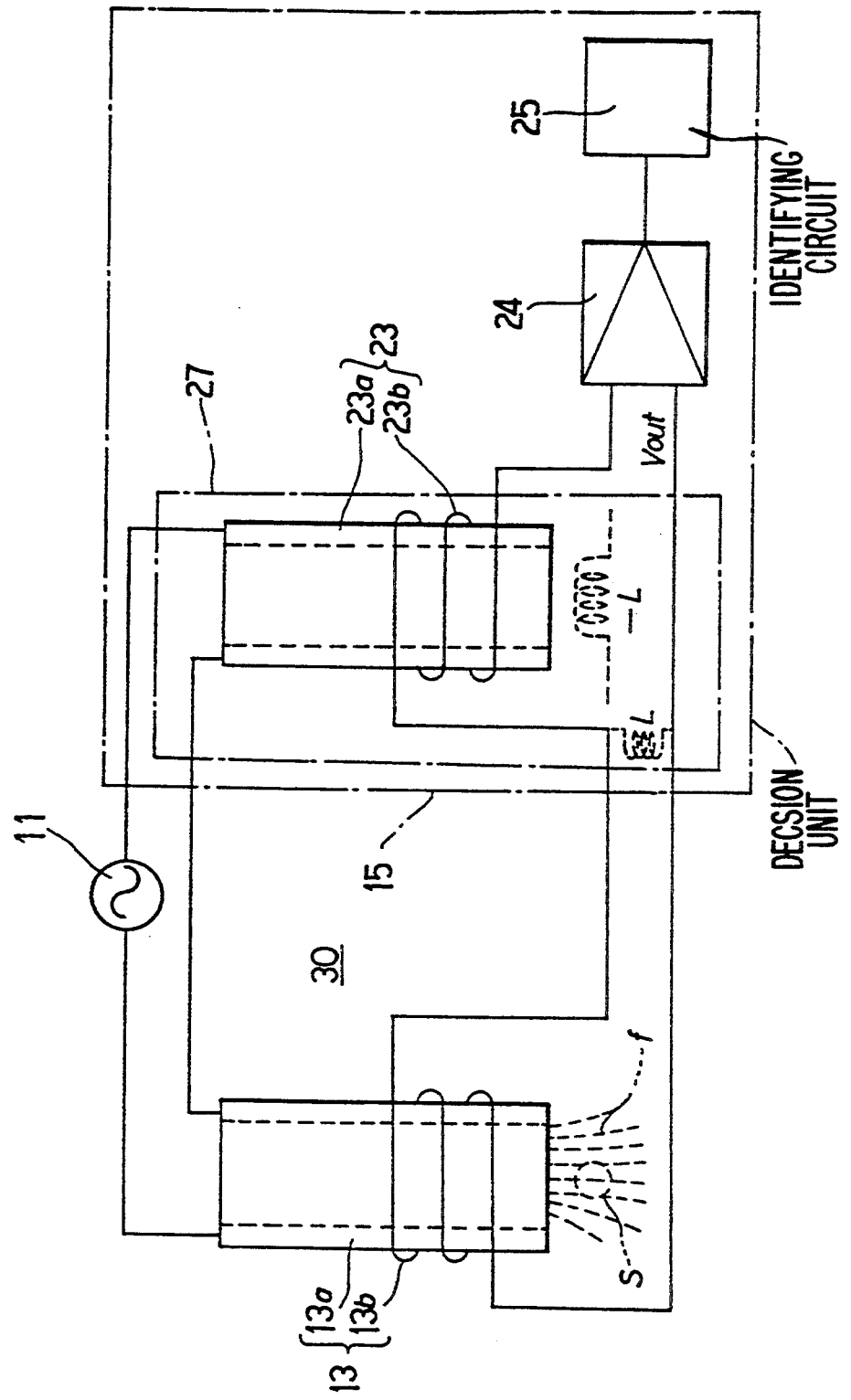
FIG. 6 is a schematic view showing a third embodiment of this invention.

There can be otherwise considered various methods for composing the inductance $-L$ of the inductor 22a in the balance circuit 22. As shown in FIG. 6 by way of example, a balance circuit 30 in which the detection coil unit 13 as specified above is connected in series to a balance inductance unit 23 having the same structure as the unit 13 except for the direction in which the coil is wound may be used. That is, the balance inductance unit 23 has an exciting coil 23a which is identical with the exciting coil 13a of the unit 13 except for the winding direction, and an induction coil 23b which is identical with the induction coil 13b of the unit 13 except for the winding direction.

In this embodiment shown in FIG. 6, the exciting coils 13a and 23a are simultaneously excited by the power source 11 to induce electromotive currents equal in quantity in the exciting coils 13a, 23a. However, the induced electromotive currents in the coils 13a, 23a are opposite in polarity to each other, because the coils 13a, 23a are wound in opposite directions. Therefore, the induced currents are cancel each other in the steady state in which the electromagnetic field (magnetic flux f) generated by the coil 13a is not affected by any other object. So long as the electromagnetic field generated by the coil 13a is in the steady state, a differential output Vout from the balance circuit 30 is kept at substantially zero. However, when an object S is placed in the electromagnetic field induced by the coil 13a, the inductance of the coil 13b varies to generate a significant differential output Vout. Thus, even delicate changes among the given objects to be inspected can be recognized accurately.

Figure 7:
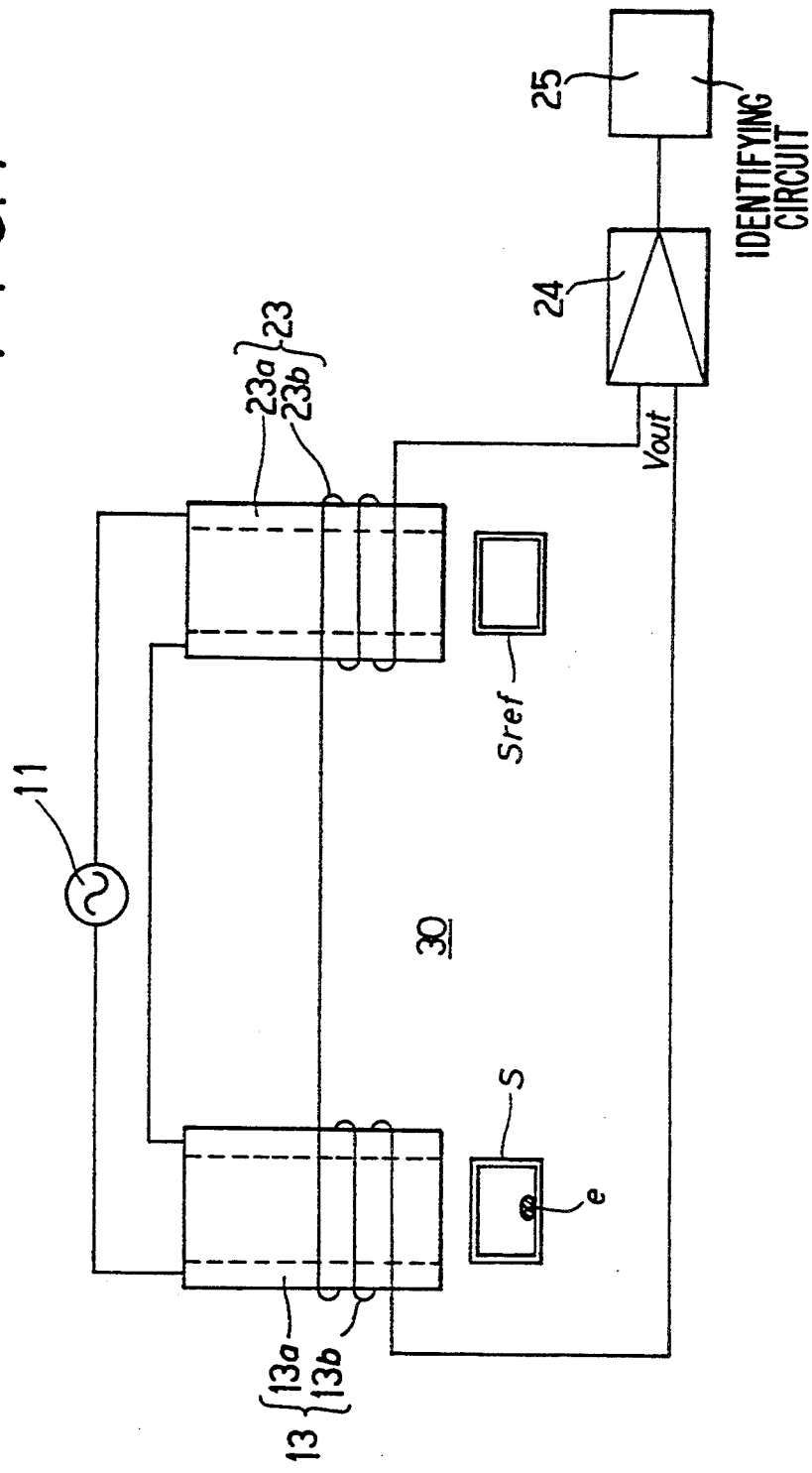
FIG. 7 is an explanatory diagram showing the state in which an object is inspected with the device of FIG. 6.

By using the inspection device shown in FIG. 6, even a fine foreign substance or defect in the object S can be readily detected with a high accuracy. For instance, an inspection for detecting a foreign substance e in a hollow object S can be carried out in such a manner that, as illustrated in FIG. 7, a standard specimen Sref is continuously placed in the electromagnetic field induced by the exciting coil 23a and the measuring object S is placed in the electromagnetic field induced by the exciting coil 13a.

In the case where no foreign substance is present in the object S, the equivalent electromotive currents which are different in polarity occur in the induction coils 13b and 23b, deriving no differential current (Vout=0) from the balance circuit 30. However, when the foreign substance e is present in the object S, the induction coils 13a, 23b assume a nonequilibrium state to give rise to an differential current (Vout>0). Thus, the existence of the foreign substance e in the object S can be recognized. It goes without saying that the object S should be located at the same relative position to the detection coil unit 13 as the relative position of the standard specimen Sref to the detection coil unit 23.

Figure 8:
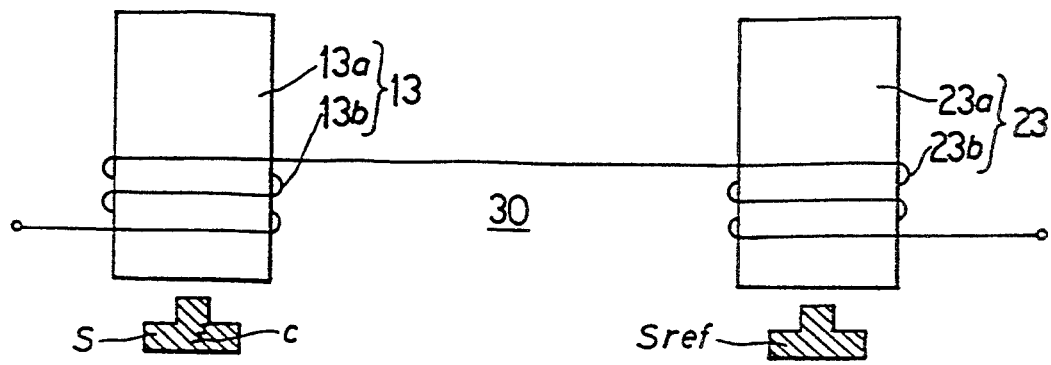
FIG. 8 is an explanatory diagram showing the state in which another object is inspected with the device of FIG. 6.

In a case of inspecting an object S of metallic material, as illustrated in FIG. 8, a standard workpiece Sref is placed in the electromagnetic field induced by the exciting coil 23a, and a product workpiece S is located in the electromagnetic field induced by the exciting coil 13a. If a defect c such as a crack exists in the object S, an eddy current occurs about the defect c in the object S and affects the electromagnetic field induced by the exciting coil 13a, to thereby break the equilibrium state of the balance circuit 30. As a result, a differential current is caused, and therefore, the defect in the object 8 can be precisely detected.

According to this inspection device, even an internal fine defect such as a fine crack and pinhole in a welded portion which is invisible from the surface of the workpiece can be reliably detected with ease.

Evaluation experiments for the inspection device of this invention were conducted by use of the detection coil unit and the balance inductance unit as described above. The detection unit and the balance inductance unit used in the experiments each included the exciting coils (13a, 23a) made by windings of 300 turns of conductive wire around a plastic bobbin having a length of 2.0 cm, inner diameter of 5.2 cm and thickness of 5 mm, and the induction coil (13b, 23b) made by winding of 300 turns of conductive wire around the exciting coil. To the exciting coils 13a, 23a, an alternating current of 0.2 kHz to 1.0 kHz and 15 volts was applied. In this case, the inductance of each exciting coil was 5.8 mH, and that of each induction coil was 6.5 mH. With this inspection device, metal nuts of 20 mm in width across corners were inspected. Consequently, a fine crack of the order of 0.1 mm in depth and 3 mm in length could be detected.

Though the detection coil unit in the aforenoted embodiment has the induction coil 13b wound around a part of the outer periphery of the exciting coil 13a, any possible structure of the coil unit may be employed if the exciting coil and the induction coil are integrally connected in a coaxial relation. The modified embodiments of this invention will be described hereinafter.

Figure 9:
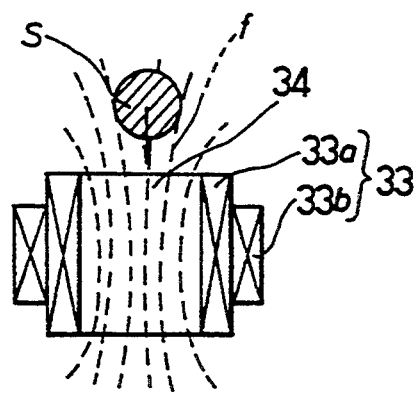
FIG. 9 is a schematic view showing a fourth embodiment of this invention.

The fourth embodiment shown in FIG. 9 has a detection coil unit 33 formed integrally of an exciting coil 33a and an induction coil 33b wound on the longitudinally central portion of the outer periphery of the exciting coil 33a. This detection coil unit 33 is advantageous in that the same electromagnetic properties involving mutual induction can be obtained at opposite end portions. Though, in the illustrated embodiment, an object S to be inspected is placed opposite to one end portion (upper end in the drawing) of the detection coil unit 33, it may be passed through the inside of the cylindrical exciting coil 33a which serves as an inspection path 34. The mutual inductance induced in the induction coil 33b varies with the transit of the object S across the inspection path 34. Thus, the object S can be inspected by analyzing the change in inductance which is consequently obtained.

Figure 10:
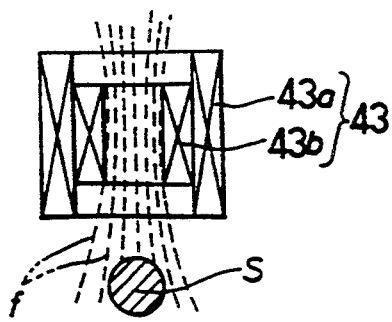
FIG. 10 is a schematic view showing a fifth embodiment of this invention.

A detection coil unit 43 shown in FIG. 10 as the fifth embodiment has an induction coil 43b integrally disposed inside an exciting coil 43a. This structure can make the size of the detection coil unit smaller.

In a detection coil unit 53 shown in FIG. 11, an exciting coil 53a and an induction coil 53b have the same outer and inner diameters and are integrally connected and arranged coaxially side by side. This detection coil unit 53 also has the same effect and function as those of the embodiments described earlier.

Shown in FIG. 12 is a detection coil unit 63 having a pair of induction coils 63b wound around the outer periphery of an exciting coil 63a. In FIG. 13, a pair of induction coils 73b are disposed inside an exciting coil 73a. In either case, the induction coils are wound in opposite directions and connected in series so as to derive a differential current in a nonequilibrium state.

In evaluation experiments actually conducted, there was used the detection coil unit 63 made by a winding of 1000 turns of wire round a plastic bobbin of 15 cm in length, 3 cm in inner diameter and 1 mm in thickness to form the exciting coil 63a, and windings of 1000 turns of wire round the outside of the exciting coil 63a to form the induction coils 63b. The exciting coil 63a was applied with an alternating current of 0.1 kHz to 1.0 kHz and 15 volts to induce an electromagnetic field (electromagnetic flux f) around the detection coil unit 63. In this case, the respective inductances of the exciting coil and induction coils were 100 mH. According to this inspection device, a small steel ball of the order of 0.1 mm in diameter could be detected.

As described above, the structure of the exciting coil and induction coil constituting the detection coil unit can be modified variously, and therefore, it is not specifically limited to the illustrated embodiments. For example, though every exciting coil in the illustrated embodiments is larger in cross-sectional area than the induction coil, this is by no means limitative, and conversely, the induction coil may be made larger in not only cross section but also in winding number and any other structure than the exciting coil as a matter of course.

It is clear from the detailed description given above that according to this invention, all sorts of objects irrespective of material including dielectric substances and magnetic substances can be inspected with a notably high accuracy and sensitivity. For instance, identification of the objects such as foods, medicinal tablets, synthetic resin products and various workpieces can be accurately effected regardless of the size of the objects. Further, according to this inspection device, abnormalities such as a defect in the measuring object can be accurately detected.

As many apparently widely different embodiments of this invention may be made without departing from the spirit and scope thereof, it is to be understood that the invention is not limited to the specific embodiments thereof except as defined in the appended claims.

What is claimed is:

1. A device for inspecting an object according to a change in electromagnetic induction, comprising:

a unitary detection coil unit having an inspection path extending therethrough through which the object to be tested is passed and consisting essentially of a first coil structure containing an exciting coil which is responsive to an alternating current applied thereto to generate an electromagnetic field that varies according to the object as the object is passed through said inspection path, and a second coil structure containing an induction coil which directly receives said electromagnetic field generated by said exciting coil and in which an electromotive current is induced responsive to said electromagnetic field generated by said exciting coil, said electromotive current denoting the electromagnetic induction of said unitary detection coil unit; and a decision unit coupled to said induction coil for receiving said electromotive current induced in said induction coil, for comparing said electromotive current with a predetermined reference value to obtain a comparison result, and for detecting an abnormality in the object to be tested according to the comparison result, wherein said second coil structure is directly fixed to said first coil structure to form said unitary detection coil unit, and wherein one of said induction coil and said exciting coil is coaxially wound around the other of said induction coil and said exciting coil, and wherein said exciting coil contained by said first coil structure is electrically insulated from said induction coil contained by said second coil structure, wherein said first coil structure is cylindrical having an inner peripheral surface and an outer peripheral surface, said inner peripheral surface of said first coil structure surrounding said inspection path, and said second coil structure is directly fixed to said first coil structure along said outer peripheral surface of said first coil structure such that said induction coil is located coaxially around said exciting coil.

2. A device as recited in claim 1, wherein said decision unit comprises:
 a comparator for comparing an output signal from said induction coil with a predetermined reference voltage and for generating a corresponding comparison signal; and,
 an identification circuit for identifying, based on said comparison signal, an object located within said electromagnetic field generated by said exciting coil.

3. A device as recited in claim 1, further comprising a balance induction unit coupled to said detection coil unit, said balance induction unit having a third coil structure which is structurally equivalent to said first coil structure and a fourth coil structure which is structually equivalent to said second coil structure, wherein said exciting coils of said detection coil unit and said balance induction unit are series coupled, and wherein said induction coils of said detection coil unit and said balance induction unit are series coupled and wound in opposite directions.

4. A device as recited in claim 1, wherein said exciting coil is wound around a bobbin to form said first coil structure, and wherein an electromagnetic shielding layer is wrapped around said first coil structure, an insulating layer is wrapped around said electromagnetic shielding layer, and said induction coil is wound around said insulating layer to form said second coil structure directly fixed to said first coil structure.

5. A device for inspecting an object according to a change in electromagnetic induction, comprising:
 a unitary detection coil unit having an inspection path extending therethrough through which the object to be tested is passed and consisting essentially of a first coil structure containing an exciting coil which is responsive to an alternating current applied thereto to generate an electromagnetic field that varies according to the object as the object is passed through said inspection path, and a second coil structure containing an induction coil which directly receives said electromagnetic field generated by said exciting coil and in which an electromotive current is induced responsive to said electromagnetic field generated by said exciting coil, said electromotive current denoting the electromagnetic induction of said unitary detection coil unit; and
 a decision unit coupled to said induction coil for receiving said electromotive current induced in said induction coil, for comparing said electromotive current with a predetermined reference value to obtain a comparison result, and for detecting an abnormality in the object to be tested according to the comparison result, wherein said second coil structure is directly fixed to said first coil structure to form said unitary detection coil unit, and wherein one of said induction coil and said exciting coil is coaxially wound around the other of said induction coil and said exciting coil, add wherein said exciting coil contained by said first coil structure is electrically insulated from said induction coil contained by said second coil structure, wherein said first coil structure is cylindrical having an inner peripheral surface and an outer peripheral surface, and said second coil structure is directly fixed to said first coil structure along said inner peripheral surface of said first coil structure such that said exciting coil is located coaxially around said induction coil, an inner peripheral surface of said second coil structure surrounding said inspection path.

* * * * *